(12) United States Patent
Avshalom et al.

(10) Patent No.: US 10,123,663 B2
(45) Date of Patent: Nov. 13, 2018

(54) METHOD FOR MANUFACTURING A SPONGE WITH INNER SOAP CAPSULE

(71) Applicants: Shimon Avshalom, Bet Shemesh (IL); Yom Tov Lipa Sardheli, Bet Shemesh (IL); Shlomo Matan Avshalom, Bet Shemesh (IL)

(72) Inventors: Shimon Avshalom, Bet Shemesh (IL); Yom Tov Lipa Sardheli, Bet Shemesh (IL); Shlomo Matan Avshalom, Bet Shemesh (IL)

(*) Notice: Subject to any disclaimer, the term of this patent is extended or adjusted under 35 U.S.C. 154(b) by 123 days.

(21) Appl. No.: 15/368,613

(22) Filed: Dec. 4, 2016

(65) Prior Publication Data

US 2018/0153355 A1    Jun. 7, 2018

(51) Int. Cl.
*A47K 7/03* (2006.01)
*A47L 13/17* (2006.01)

(52) U.S. Cl.
CPC ............... *A47K 7/03* (2013.01); *A47L 13/17* (2013.01)

(58) Field of Classification Search
CPC .............. A47K 7/00; A47K 7/03; A47L 13/17
See application file for complete search history.

(56) References Cited

U.S. PATENT DOCUMENTS

| | | | | |
|---|---|---|---|---|
| 1,386,041 A | * | 8/1921 | Wilson | A47K 7/03 15/244.3 |
| 3,014,233 A | * | 12/1961 | Gibbons | A47L 13/03 15/229.12 |
| 3,977,452 A | * | 8/1976 | Wright | A45C 11/24 15/209.1 |
| 4,457,643 A | * | 7/1984 | Caniglia | A47K 7/03 401/200 |
| 4,674,237 A | * | 6/1987 | Sullivan | A47L 13/17 451/523 |
| 5,671,498 A | * | 9/1997 | Martin | A47K 7/03 15/104.93 |
| 6,783,294 B2 | * | 8/2004 | Duden | A45D 44/00 401/196 |
| 7,423,003 B2 | * | 9/2008 | Volpenhein | C11D 3/222 510/281 |
| 9,867,508 B2 | * | 1/2018 | Weinberg | A47K 7/03 |
| 2002/0197094 A1 | * | 12/2002 | Gruenbacher | A47K 7/03 401/133 |
| 2012/0233795 A1 | * | 9/2012 | Avshalom | A47K 7/03 15/104.93 |
| 2014/0366294 A1 | * | 12/2014 | Roe | A47L 13/17 15/104.93 |

* cited by examiner

*Primary Examiner* — Christopher R Harmon

(57) ABSTRACT

A method of manufacturing a sponge with inner capsule that contains soap. The method includes: Providing a scouring pad coating sleeve, a first and second strip of inner sponge, and a nylon sleeve which is divided into a serial of capsules. Providing a tray that ended with a hollow pipe and placing on it the first strip, then the nylon sleeve and then the second strip. Dressing up the scouring sleeve on the hollow pipe. Pushing the strips together with the nylon sleeve inside the hollow pipe until their front goes out through the hollow pipe, holding them together and pulling them outside of the hollow pipe until they are positioned inside the scouring sleeve. Welding and cutting the scouring sleeve to pieces according the size of the capsules.

1 Claim, 4 Drawing Sheets

METHOD FOR MANUFACTURING A SPONGE WITH INNER SOAP CAPSULE

TECHNICAL FIELD

The present invention refers to a method for manufacturing a sponge for cleaning utensils that includes an inner capsule that contains soap.

BACKGROUND ART

Many people use wash sponges, for instance to wash dishes, as a bath sponge, and for cleaning and washing various accessories. It is known that there are sponges that contain a relatively pliable capsule that contains liquid soap that flows out of the capsule into the sponge through small holes in the capsule. In this case, squeezing the sponge actually squeezes the capsule, causing liquid soap to flow from the inner capsule out into the sponge. This kind of sponges is not perfect since the flow of liquid soap from the capsule into the sponge is uncontrolled and even when the sponge is already sudsy and saturated with soap, soap continues to flow from the capsule into the sponge due to the pressure the user's hand applies to the sponge when in use. The present invention offers an improved sponge with a capsule that operates according to the principles of the aforementioned method, but which introduces an innovation that solves the problem inherent in such sponges. In addition, the present invention discloses an easy method for manufacturing said sponge.

THE INVENTION

The main and primary objectives of the present invention are to provide a method for manufacturing of a wash sponge with an inner capsule that contains soap. Another objective of the present invention is to provide said manufacturing method wherein while using said sponge there is no significant flow of liquid soap into the sponge when the user's hand applies pressure to the sponge during its use and that only intentional squeezing of the sponge leads to the flow of liquid soap into the sponge.

Figure 1:
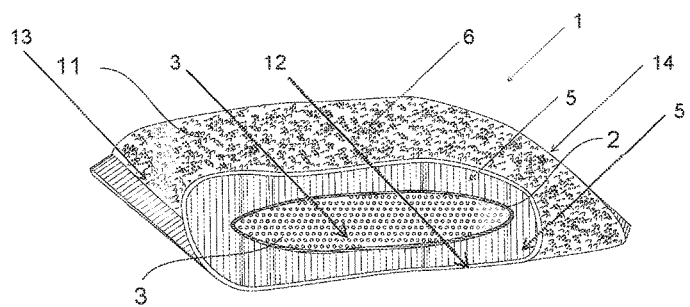
FIG. 1 depicts the sponge (1) with the inner capsule (2) that contains soap (3).

The present invention refers to a method of manufacturing the sponge (1) that includes a scouring pad coating (6), one or two inner sponge layers (5) and an inner capsule (2) that contains soap (3). FIG. 1 depicts a cross-section of the sponge (1) that contains the inner capsule (2) with soap (3).

The sponge (1) can be one of a wide variety of existing sponges, such as sponges designed for washing dishes, bath sponges, and a wide variety of sponges for various uses. For the sake of fluency, the term "wash sponge" will hereinafter refer to the entire variety of said sponges intended for the variety of aforementioned uses. The sponge (1) has the general shape of a flattened rectangular cube having relatively wide top (11) and bottom (12) sides and two sided narrow sides (13) (14). Note: the terms top side and bottom side refer only to the larger and wider sides of the sponge (1) as depicted in the drawings, whereas in reality, none of the sides of the sponge (1) and the capsule (2) are designated as being the top side.

The capsule (2) is in fact a sealed packet with one or more holes (4) through which the soap (3) flows from the capsule (2) into the inner sponge layers (5) and to the scouring pad coating (6). The capsule (2) is naturally smaller than the general size of the sponge (1). The capsule (2) is made from a pliable material so that squeezing the capsule causes the soap to flow out through the holes in the capsule. The capsule can and should be made of rubber or silicone, although any material that can be squeezed by an external force can be used to manufacture the capsule (2). Thus, for instance, materials such as those used to manufacture inner tubes of bicycle tires can be used to manufacture the capsule.

Figure 2:
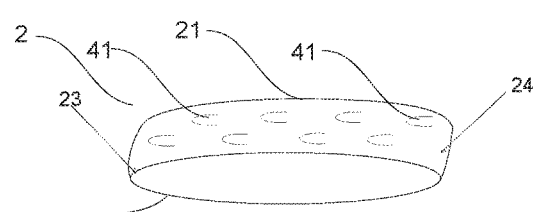
FIG. 2 depicts the capsule (2) with holes (4) in closed position.

The capsule (2) has the general shape of a flattened rectangular cube, possibly corresponding with the external shape of the sponge, as depicted for instance in FIG. 2. The capsule (2) has relatively wide top (21) and bottom (22) sides. Note: the terms top side and bottom side refer only to the larger and wider sides of the capsule (2) as depicted in the drawings, whereas in reality, none of the sides of the sponge (1) and the capsule (2) are designated as being the top side. Naturally, it is recommended that the capsule be made of a single integral piece.

The holes (4) in the capsule (2): The capsule (2) has one or more holes (4), although it is recommended that the capsule (2) have several holes, on the wide top and bottom sides (21) (22) of the capsule, as depicted for instance in FIG. 2. The main innovation of the present invention is that the hole (4) is structured such that when pressure is applied, mainly vertical pressure, on the wide top and bottom sides (11) (12) of the sponge (1) and by that also on the wide top and bottom sides (21) (22) of the capsule (2), there is no significant flow of soap through the holes (4) from the capsule into the sponge and in fact such vertical pressure closes the holes (4). On the other hand, when the user holds the sponge (1) and applied horizontal pressure to the sided narrow sides (13) (14) of the sponge (1) and by that to the sided narrow sides (23) (24) of the capsule (2), it cause the opening of the holes (4) and soap flows from the capsule through the holes into the sponge. The innovative structure of the holes (4) enables the user to control the flow of soap (3) from the capsule into the sponge. In other words, the holes (4) serve as a kind of valve.

Figure 3:
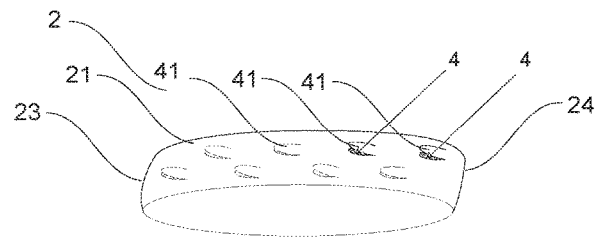
FIG. 3 depicts the capsule (2) with holes (4) in open position.

Design and structure of the hole (4): The hole (4) is made by making a small circumferential cut in the wide side of the capsule. The cut is made in an incomplete manner such that the cut flap (41) remains attached to the capsule, as depicted for instance in FIGS. 2 and 3. The cut part (41), hereinafter referred to as "the flap", remains attached to the capsule along one section. When no pressure is applied on the capsule, the flap (41) is in its original and normal position just as before the cut, so that in fact the hole is not visible and is closed, thus preventing the soap from flowing out through it. FIG. 2 depicts the holes (4) with closed flaps (41) whereas Drawing No. 3 depicts the holes (4) with open flaps (41).

Incidental pressure on the sponge: When the user squeezes the sponge, applying vertical pressure on the wide sides of the sponge, and by that also on the wide sides of the capsule—pressure that is applied naturally while using the sponge, then the sponge (1) itself compresses onto the wide side (21) (22) of the capsule (2) and the sponge actually presses downward on the flaps (41) causing them to close the holes (4) and preventing any significant flow of soap out of the capsule.

Intentional pressure on the sponge: When the user squeezes the sponge, exerting horizontal pressure on the narrow sides of the capsule, pressure that is not exerted naturally during the use of the sponge, then the flaps (41) are pushed upward and the holes (4) open, enabling the soap to flow out of the capsule. Thus, the user can control the flow of soap out of the capsule into the sponge in a good and effective manner.

Figure 4:
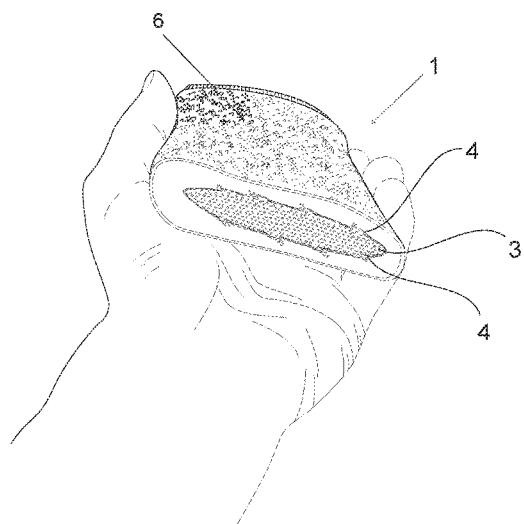
FIG. 4 depicts the sponge (2) with the inner capsule (2) that contains soap (3) being squeezed.

The holes (4) can have a variety of shapes with the common property that squeezing the narrow sides (23) (24) of the capsule (2) causes the holes (4) to open and the soap to flow out. The hole (4) can also be a simple cut that, due to the thickness of the capsule's side, opens when pressure is applied to the narrow sides of the capsule, as depicted for instance in FIG. 4. The soap (3) within the capsule (2) can be in a variety of states of matter, although it is preferable that it be a gel or even a relatively viscous liquid, and the size of the holes should correspond to the viscosity of the soap (3).

As mentioned in the present application, the capsule (2) can be made of a variety of pliable materials. One such material is a nylon bag, which can function as a capsule (2) as required for the product, subject of the invention. Nylon bags of various thicknesses can be used, although the inventor recommends that they be 0.25 mm. thick. The nylon bag used should be perforated as described in the application and should have between six and ten holes (4) on each side. The diameter of such holes (4) should be approximately 0.01 mm. When the sponge (1) contains a capsule (2) made of a nylon bag as described above, with the aforementioned thickness and with holes (4) with the aforementioned diameter, then the application of normal pressure, i.e. the pressure applied by an average use on the sponge (1) when using it to wash dishes, for instance, will not cause significant flow of soap from the capsule (2). When, however, stronger and intentional pressure is applied to the said sponge (1) containing the said nylon bag capsule (2), soap will flow from the capsule (2), enabling effective and good use of the sponge (1).

The method of manufacturing the sponge (1): The present invention relates to the manufacturing method of the sponge (1). The manufacturing of the sponge (1) includes the following steps and providing the following materials:

First, providing a sleeve (600) of the scouring pad coating (6), one or two strips (500) of the inner sponge layers (5), and a nylon sleeve (200) which is divided into a serial of capsules (2) that each of them filled with soap (3) wherein each capsule is divided from the adjacent capsule by a divisional welded strip (28) and wherein each divisional welded strip (28) includes one or more tunnels (29) that enable the soap (3) to move from one capsule to the adjacent one. The method of manufacturing a long nylon sleeve, which is divided to capsules filled with materials, is known and used for example for manufacturing small ketchup bags. Therefore there is no need to describe such method, which is known to experts in the field, but only to specify that when welding and closing the divisional welding strips (28) it is recommended to use heating plates that have one or more slits for creating the tunnels (29) that enable the soap (3) to move from one capsule (2) to the adjacent one while pressing on the nylon sleeve (200).

Figure 5:
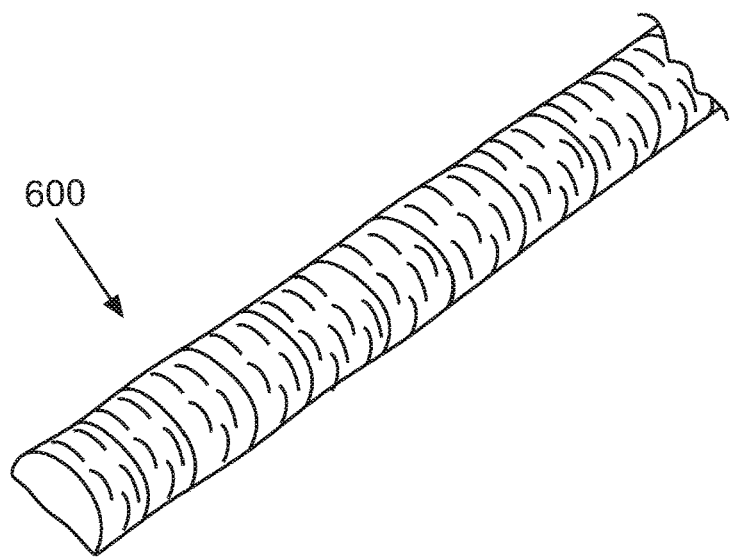
FIG. 5 depicts the sleeve of the scouring pad coating (600).
Figure 6:
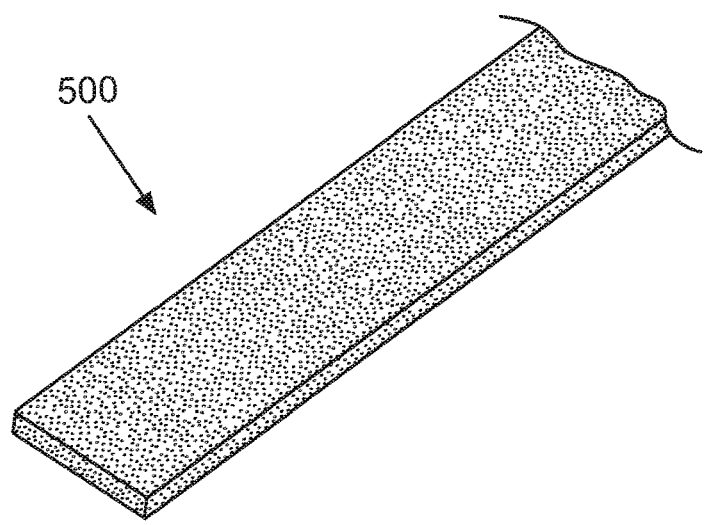
FIG. 6 depicts the strip of the inner sponge layers (500).
Figure 7:
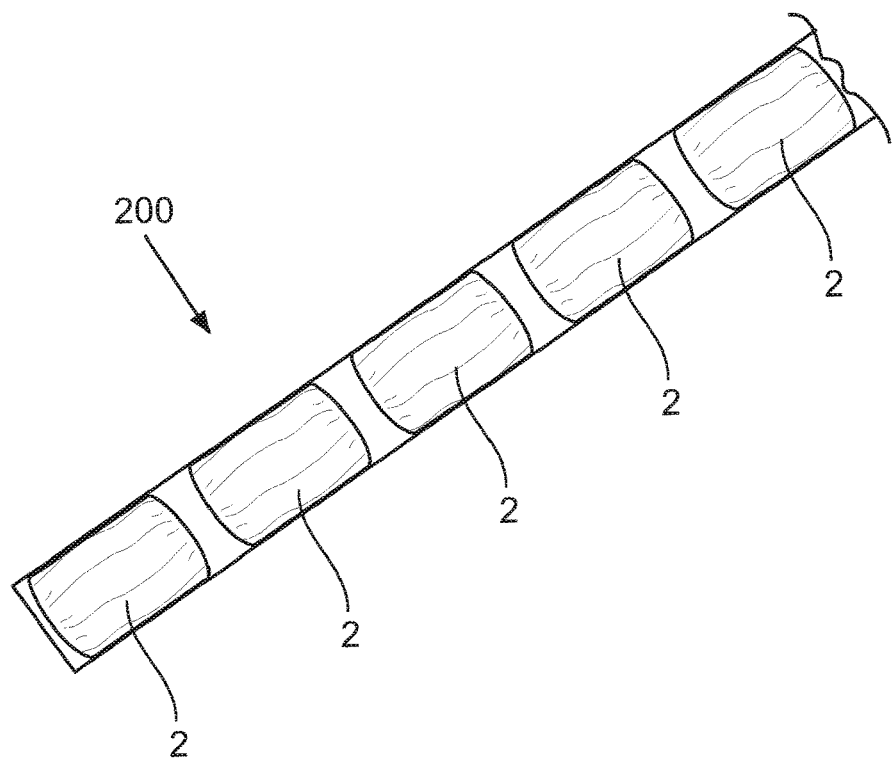
FIG. 7 depicts the nylon sleeve which is divided into a serial of capsules (200) filled with soap (3).
Figure 8:
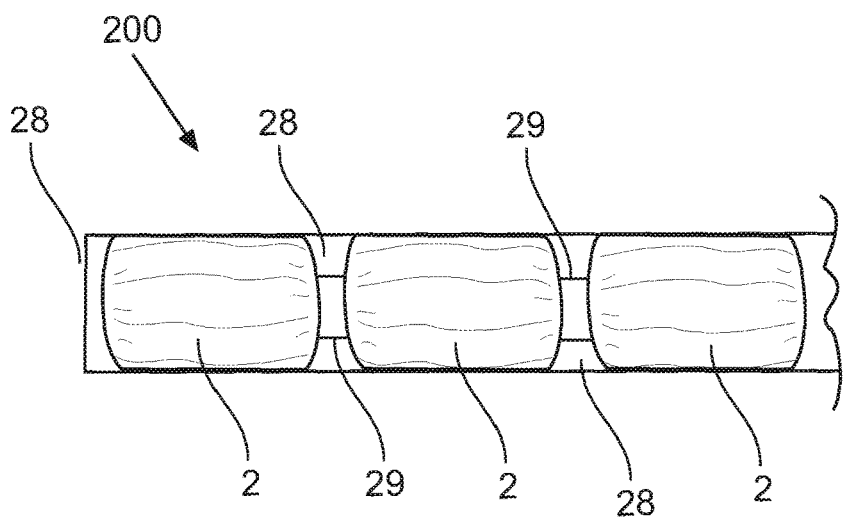
FIG. 8 depicts part of the nylon sleeve (20) showing the divisional welding strips (28) and the tunnels (29).

It is understood and recommended that said sleeve (600), strips (500) and nylon sleeve (200) will be in the same length. FIG. 5 depicts the sleeve of the scouring pad coating (600); FIG. 6 depicts the strip of the inner sponge layers (500); and FIG. 7 depicts the nylon sleeve which is divided into a serial of capsules (200) filled with soap (3); FIG. 8 depicts part of the nylon sleeve (20) showing the divisional welding strips (28) and the tunnels (29).

Figure 9:
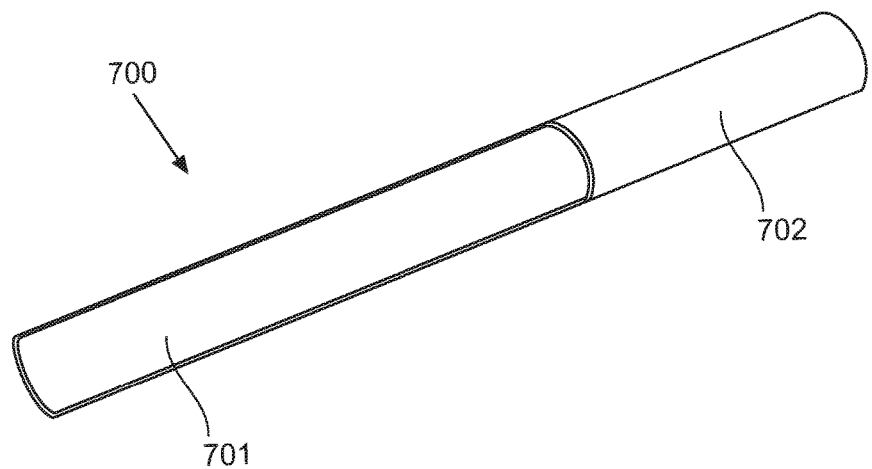
FIG. 9 depicts the assembling apparatus (700).

Second, providing an assembling apparatus (700) that includes a tray (701) that ended with a hollow pipe (702), as depicts for example in FIG. 9. The length of the tray (701) should be corresponding with the length of the sleeves (600) and (200) and the strips (500). It is possible to make this assembling apparatus (700) by using a long hollow pipe and cutting its upper part of part of it.

Figure 10:
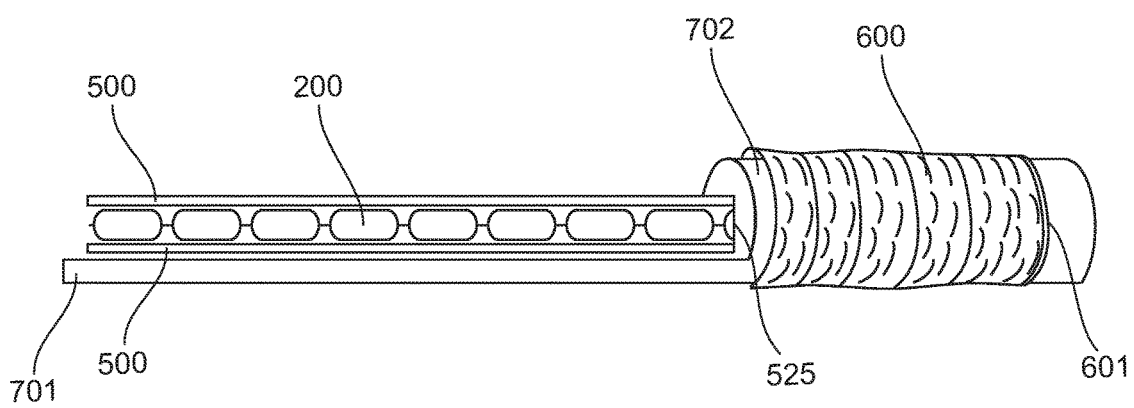
FIG. 10 depicts the assembling apparatus (700) with two inner sponge layer (500), a nylon sleeve of the serial of capsules (200) and the sleeve of the scouring pad coating (600).

Third, to place on the tray (701) one strip of the inner sponge layer (500; then, to place on said strip (500) the nylon sleeve of the serial of capsules (200); then to place on the nylon sleeve (200) a second strip of the inner sponge layer (500); and then to dress up the sleeve of the scouring pad coating (600) on the hollow pipe (702); as described schematically in FIG. 10.

Fourth, to push the strips (500) and the nylon sleeve (200), which is positioned between them, inside the hollow pipe (702) until their front (525) goes out through the hollow pipe (702), and then holding together said front (525) of the strips (500) and nylon sleeve (200) together with the front (601) of the sleeve (600) and pulling them together outside of the hollow pipe (702) wherein the strips (500) and the nylon sleeve (200) are positioned inside the sleeve (600) (hereinafter "the ready sleeve (6525)".

Fifth, pressing on the ready sleeve (6525) and by that the soap (3) is spread nearly equally in the capsules (2) and any extra soap can move from one capsule to the adjacent one through the tunnels (29). Then, welding and cutting the ready sleeve (6525) to pieces according the size of the capsules (2) and by that to make the final ready for use sponge (1).

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method of manufacturing a washing sponge wherein said washing sponge includes an inner capsule that contains soap, that has one or more holes; wherein said washing sponge and capsule have wide top and bottom sides and two sided narrow sides; wherein said capsule is made of a pliable material that can be squeezed and is designed as a sealed packet with holes; wherein said holes are made by cutting the side of the capsule such that the holes open when horizontal pressure is applied to the sided narrow sides of the washing sponge and remain sufficiently closed when vertical pressure is applied to said wide top and bottom sides of the washing sponge; wherein said horizontal pressure can be made by the user while pressing on said sided narrow sides of the washing sponge and wherein said vertical pressure can be made by the user while pressing on said wide top and bottom sides of the washing sponge;

wherein said manufacturing method of said washing sponge includes the following steps and providing the following materials:

providing a sleeve of a scouring pad coating, a first strip of inner sponge layer and a second strip of inner sponge layer, and a nylon sleeve which is divided into a serial of said capsules that each of them filled with soap wherein each capsule is divided from the adjacent capsule by a divisional welded strip and wherein each divisional welded strip includes one or more tunnels that enable the soap to move from one capsule to the adjacent one;

providing an assembling apparatus that includes a tray that ended with a hollow pipe;

Placing on the tray the first strip of the inner sponge layer; placing on said strip the nylon sleeve of the serial of capsules; placing on the nylon sleeve the second strip of the inner sponge layer; dressing up the sleeve of the scouring pad coating on the hollow pipe;

Pushing the first and the second strips of the inner sponge layers and the nylon sleeve, which is positioned between them, inside the hollow pipe until their front goes out through the hollow pipe, and then holding together said front of the first and second strips of inner sponge layers and nylon sleeve together with the front of the sleeve of a scouring pad coating and pulling them together outside of the hollow pipe wherein the first and second strips of inner sponge layers and the nylon sleeve are positioned inside the sleeve of a scouring pad coating;

pressing on the sleeve of a scouring pad coating when said first and second strips of inner sponge layers and said nylon sleeve are positioned inside the sleeve of a scouring pad coating whereby any extra soap in each capsule can move from any capsule to the adjacent one through the tunnels;

welding and cutting the sleeve of a scouring pad coating when said first and second strips of inner sponge layers and said nylon sleeve are positioned inside the sleeve of a scouring pad coating to pieces according the size of the capsules and by that to make the washing sponge.

\* \* \* \* \*